United States Patent
Hamilton, II et al.

(10) Patent No.: US 11,416,567 B2
(45) Date of Patent: Aug. 16, 2022

(54) METHOD AND SYSTEM FOR INDIVIDUALIZED PRESENTATION OF PRIORITIZED INFORMATION

(71) Applicant: Optum, Inc., Minnetonka, MN (US)

(72) Inventors: Rick A. Hamilton, II, Minneapolis, MN (US); Kathleen E. Uske, Basking Ridge, NJ (US); Patrick J. Hafford, Basking Ridge, NJ (US); Scott E. Washburn, Basking Ridge, NJ (US)

(73) Assignee: Optum, Inc., Minnetonka, MN (US)

( * ) Notice: Subject to any disclaimer, the term of this patent is extended or adjusted under 35 U.S.C. 154(b) by 49 days.

(21) Appl. No.: 16/136,890

(22) Filed: Sep. 20, 2018

(65) Prior Publication Data
US 2020/0097606 A1    Mar. 26, 2020

(51) Int. Cl.
| | | |
|---|---|---|
| *G06F 15/16* | (2006.01) | |
| *G06F 16/9535* | (2019.01) | |
| *G16H 20/10* | (2018.01) | |
| *G06F 16/907* | (2019.01) | |
| *G06F 16/9038* | (2019.01) | |

(52) U.S. Cl.
CPC ........ *G06F 16/9535* (2019.01); *G06F 16/907* (2019.01); *G06F 16/9038* (2019.01); *G16H 20/10* (2018.01)

(58) Field of Classification Search
CPC ............... G06F 16/9535; G06F 16/907; G06F 16/9038; G16H 20/10
See application file for complete search history.

(56) References Cited

U.S. PATENT DOCUMENTS

| | | |
|---|---|---|
| 5,845,255 A | 12/1998 | Mayaud |
| 9,886,556 B2 | 2/2018 | Booth et al. |
| 2005/0060188 A1 | 5/2005 | Valley |
| 2008/0109260 A1 | 5/2008 | Roof |

(Continued)

OTHER PUBLICATIONS

Definition of Vital Signs by Merriam-Webster, https://www.merriam-webster.com/dictionary/vital%20signs. pp. 1-4.*

(Continued)

*Primary Examiner* — Alex Gofman
*Assistant Examiner* — Shelly X Qian
(74) *Attorney, Agent, or Firm* — Alston & Bird LLP

(57) ABSTRACT

A computing entity storing a user profile data store and an informational content data store receives new event information corresponding to a user. The new event information is associated with a user identifier and is provided via user interaction with an interactive user interface (IUI). Using the user identifier, the computing entity identifies and accesses a user profile from the user profile data store that comprises profile information corresponding to the user. Based on the new event information and/or the profile information stored in the user profile, the computing entity prioritizes a plurality of informational content items stored in the informational content data store. Based on the prioritization of the plurality of informational content items, the computing entity selects one or more informational content items that are of high priority for the user and provides a selected informational content item for presentation to the user via the IUI.

17 Claims, 9 Drawing Sheets

(56) References Cited

U.S. PATENT DOCUMENTS

| | | | | |
|---|---|---|---|---|
| 2012/0253139 | A1* | 10/2012 | Maman | G06F 19/3456 600/300 |
| 2012/0313785 | A1* | 12/2012 | Hanson | A61J 7/049 340/573.1 |
| 2015/0205919 | A1 | 7/2015 | Robertson et al. | |
| 2015/0370999 | A1* | 12/2015 | Carpenter | G16H 10/60 705/2 |
| 2015/0379205 | A1* | 12/2015 | Evans | G16H 10/60 705/3 |

OTHER PUBLICATIONS

"10 Best iOS OCR Scanning Apps To Convert Image to Text," Mashtips, Dec. 22, 2018, 7 pages, [online], [Retrieved from the Internet Aug. 13, 2019] <https://mashtips.com/ocr-scanner-ios-apps/>.

"America's Health Literacy: Why We Need Accessible Health Information," U.S. Department of Health & Human Services, 8 pages, [online], [Retrieved from the Internet Aug. 13, 2019]<https://health.gov/communication/literacy/issuebrief/>.

"Quick Guide to Health Literacy-Fact Sheet: Health Literacy Basics," 4 pages, [online], [Retrieved from the Internet Aug. 13, 2019]<https://health.gov/communication/literacy/quickguide/factsbasic.htm>.

"Text Fairy (OCR Text Scanner)—Apps On Google Play," 3 pages, [online], [Retrieved from the Internet Aug. 13, 2019] <https://play.google.com/store/apps/details?id=com.renard.ocr>.

Brown, Marie T. et al., "Medication Adherence: WHO Cares?,"Mayo Clinic Proceedings, Apr. 2011, vol. 86, No. 4, pp. 304-314, [Retrieved from the Internet Aug. 13, 2019]<https://www.ncbi.nlm.nih.gov/pmc/articles/PMC3068890/>.

Charlesworth, Christina J. et al., "Polypharmacy Among Adults Aged 65 Years and Older In The United States 1988-2010," The Journals of Gerontology Series A: Biological Sciences and Medical Sciences, Mar. 1, 2015, vol. 70, No. 8, pp. 989-995, [Retrieved from the Internet Aug. 13, 2019]<https://academic.oup.com/biomedgerontology/article/70/8/989/2947682>.

Colino, Stacey, "The Widespread Problem of Low Health Literacy," U.S. News & World Report, Apr. 6, 2016, 8 pages, [online], [Retrieved from the Internet Aug. 13, 2019]<https://health.usnews.com/health-news/patient-advice/articles/2016-04-06/the-widespread-problem-of-low-health-literacy>.

Lockwood, Will, "QR Codes: A Digital Avenue For PMI," ComputerTalk, vol. 33, No. 3, May/Jun. 2013, pp. 12-14.

Macleod, Stephanie et al., "The Impact Of Inadequate Health Literacy On Patient Satisfaction, Healthcare Utilization, and Expenditures Among Older Adults," Geriatric Nursing, Jul. 2017, vol. 38, Issue 4, pp. 334-341, [Retrieved from the Internet Aug. 13, 2019]<https://www.sciencedirect.com/science/article/pii/S0197457216302981?via%3Dihub>.

Schindler, Esther et al., "The Best Mobile Scanning Apps For 2019," PCMag.com, Jan. 23, 2018, (21 pages), [Retrieved from the Internet Aug. 13, 2019]<https://www.pcmag.com/roundup/349681/the-best-mobile-scanning-apps>.

Tseng, Ming-Hseng et al., "A Cloud Medication Safety Support System Using QR Code and Web Services For Elderly Outpatients," Technology and Health Care, vol. 22, No. 1, (2014), pp. 99-113, [Retrieved from the Internet Aug. 13, 2019]<https://content.iospress.com/articles/technology-and-health-care/thc00778>.

Lee, Yun-Mi et al. "Impact Of Health Literacy On Medication Adherence In Older People With Chronic Disease," Collegian, vol. 24, Issue 1, pp. 11-18, Feb. 1, 2017, DOI: 10.1016/j.colegn.2015.08.003.

* cited by examiner

METHOD AND SYSTEM FOR INDIVIDUALIZED PRESENTATION OF PRIORITIZED INFORMATION

FIELD

Various embodiments relate generally to an interactive user interface configured to provide a user with informational content items that are prioritized specifically for the user. For instances, as an example embodiment, medical information can be provided to interactive user interface configured to provide a user with informational content items that are prioritized based on medical information corresponding to a user.

BACKGROUND

In the age of the Internet, the amount of informational content available to users tends to be overwhelming large. For example, in the medical context, even if a user is looking for information regarding a particular medication or particular medical procedure, the user may come across a significant amount of information that may not be relevant to that user. As such, a user may miss information that is of particular importance to that user.

Accordingly, there is a latent need for a rigorous methodology that can determine/identify, customize, and prioritize user information to be presented via an interactive user interface. Through applied effort, ingenuity, and innovation, the inventors have developed systems and methods that provide such embodiments. Some examples of these solutions are described in detail herein.

BRIEF SUMMARY

Various embodiments provide methods, apparatuses, computer program products, systems, and/or the like that provide for providing a user with informational content items that are prioritized specifically for a user in a variety of contexts and settings. While the following is described in the medical context for aid in understanding the invention, the various embodiments are not limited to the medical context.

In one embodiment, a prioritized information IUI is provided configured to receive new event information/data. Based on the new event information/data and/or profile information/data stored in user profile corresponding to the user, a plurality of informational content items may be prioritized. In various embodiments, informational content items may be white papers, how-to guides, instructional videos, and/or other appropriate content. For example, each informational content item may be associated with one or more content indicators. Based on the matching of the one or more content indicators associated with an informational content item with the new event information/data and/or profile information/data stored in the user profile corresponding to the user, it may be determined if the informational content item is relevant to the user. The informational content items that are relevant to the user may then be prioritized based on one or more weights corresponding to the one or more content indicators, an order of the informational content items, and/or the like. One or more relevant informational content items may then be provided to a user via the IUI or other presentation method (e.g., via an email and/or the like) such that the informational content items that were deemed to have a higher priority are prominently provided. Thus, various embodiments provide an improved IUI that provides a user with easier access to information/data that is relevant to a particular user.

According to one aspect of the present invention, a method for providing personalized prioritized informational content to a user is provided. In an example embodiment, the method comprises receiving, by a prioritization computing entity, new event information corresponding to a user. The prioritization computing entity comprises at least one processor, a first memory storing a user profile data store, a second memory storing an informational content data store, and a network interface configured to communicate via at least one network. The new event information is associated with a user identifier. The new event information is provided to the prioritization computing entity responsive to (i) the new event information being provided to a user computing entity via user interaction with a prioritized information interactive user interface or (ii) processing of user-specific information by another computing entity. Based on the user identifier, identifying and accessing, by the prioritization computing entity, a user profile (a) from the user profile data store and (b) comprising profile information corresponding to the user. Based on at least one of (a) the new event information or (b) the profile information stored in the user profile, prioritizing, by the prioritization computing entity, a plurality of informational content items stored in the informational content data store. Based on the prioritization of the plurality of informational content items, selecting, by the prioritization computing entity, one or more informational content items that are of high priority for the user. The method further comprises providing, by the prioritization computing entity, at least one of the selected one or more informational content items for presentation to the user via the prioritized information interactive user interface.

According to another aspect of the present invention, an apparatus is provided. In an example embodiment, the apparatus comprises at least one processor, at least one memory including computer program code for one or more programs, and a network interface configured to communicate via at least one network. The at least one memory and the computer program code are configured to, with the at least one processor, cause the apparatus to at least store, in the at least one memory, (a) a user profile data store and (b) an informational content data store; receive, via the network interface, new event information corresponding to a user, wherein (a) the new event information is associated with a user identifier and (b) the new event information is provided to the prioritization computing entity responsive to (i) the new event information being provided to a user computing entity via user interaction with a prioritized information interactive user interface or (ii) processing of user-specific information by another computing entity; based on the user identifier, identify and access a user profile (a) from the user profile data store and (b) comprising profile information corresponding to the user; based on at least one of (a) the new event information or (b) the profile information stored in the user profile, prioritize a plurality of informational content items stored in the informational content data store; based on the prioritization of the plurality of informational content items, select one or more informational content items that are of high priority for the user; and provide at least one of the selected one or more informational content items for presentation to the user via the prioritized information interactive user interface.

According to yet another embodiment, a computer program product is provided. In an example embodiment, the computer program product comprises at least one non-transitory computer-readable storage medium having computer-executable program code portions stored therein. The computer-executable program code portions comprise program code instructions. The computer program code instructions, when executed by a processor of a computing entity, are configured to cause the computing entity to at least store, in at least one computer-readable memory, (a) a user profile data store and (b) an informational content data store; receive new event information corresponding to a user, wherein (a) the new event information is associated with a user identifier and (b) the new event information is provided to the prioritization computing entity responsive to (i) the new event information being provided to a user computing entity via user interaction with a prioritized information interactive user interface or (ii) processing of user-specific information by another computing entity; based on the user identifier, identify and access a user profile (a) from the user profile data store and (b) comprising profile information corresponding to the user; based on at least one of (a) the new event information or (b) the profile information stored in the user profile, prioritize a plurality of informational content items stored in the informational content data store; based on the prioritization of the plurality of informational content items, select one or more informational content items that are of high priority for the user; and provide at least one of the selected one or more informational content items for presentation to the user via the prioritized information interactive user interface.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 4:
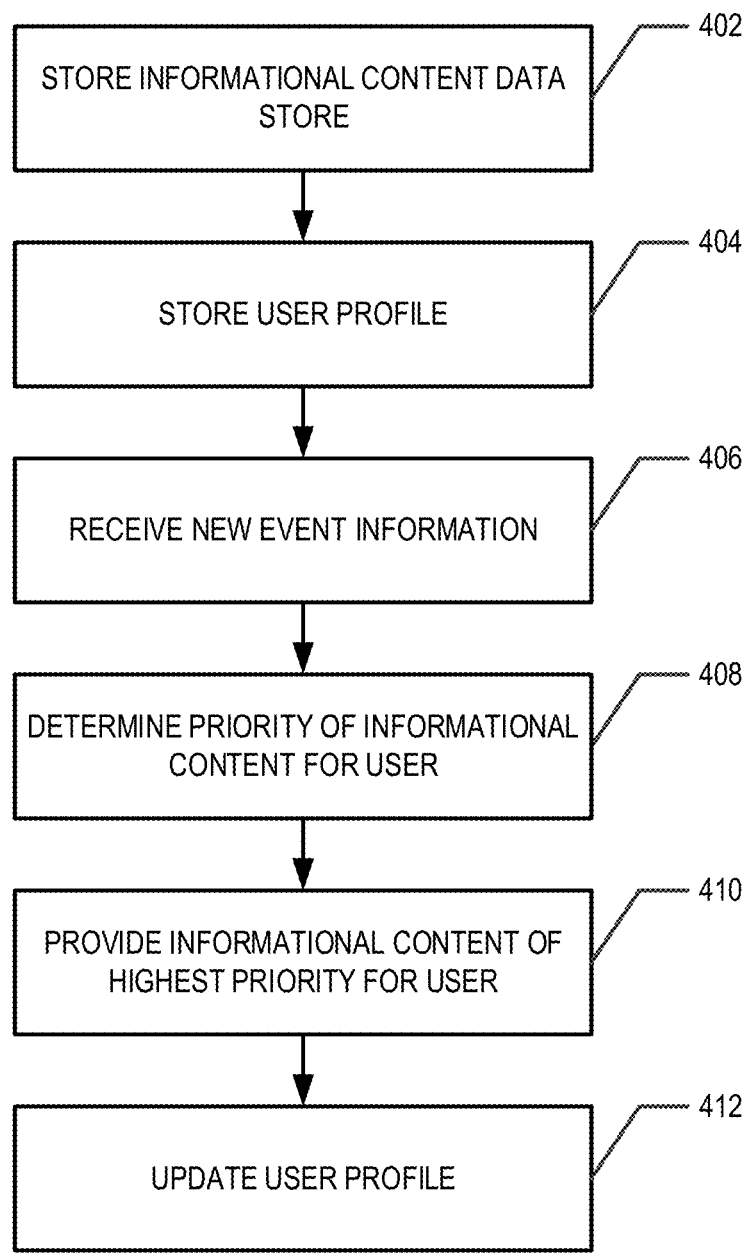
Figure 5:
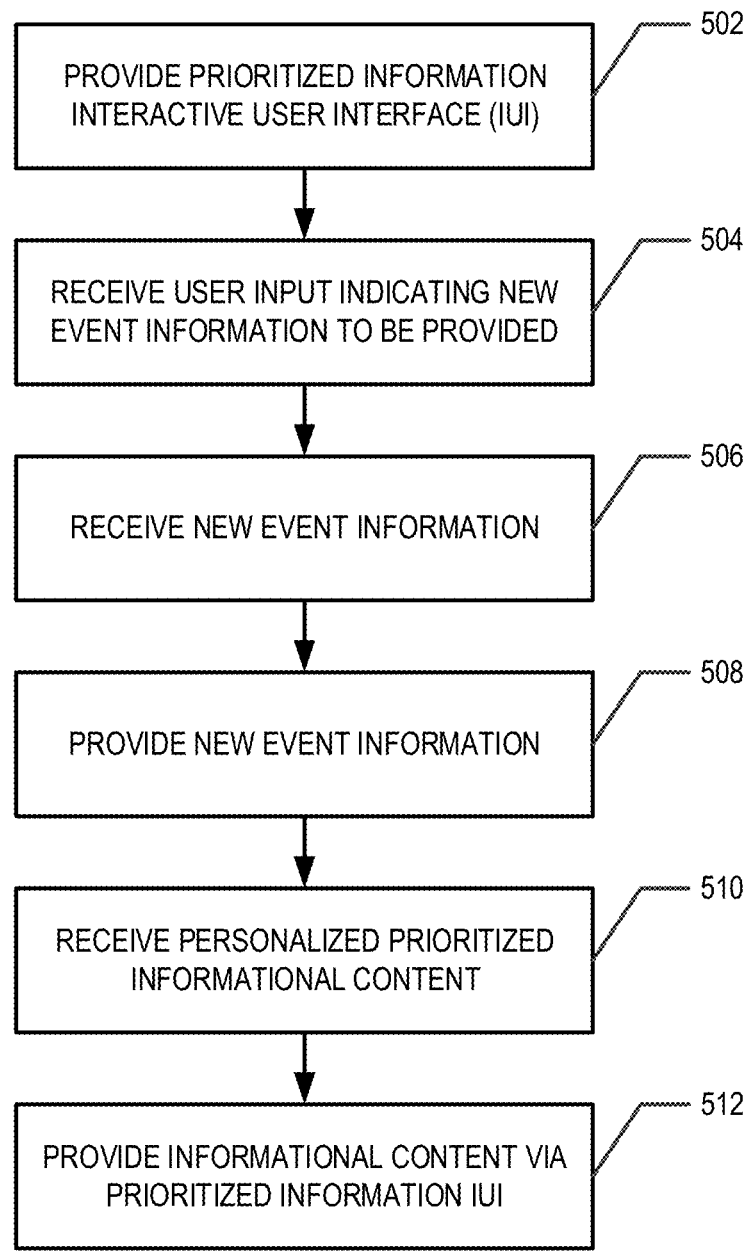
Figure 6:
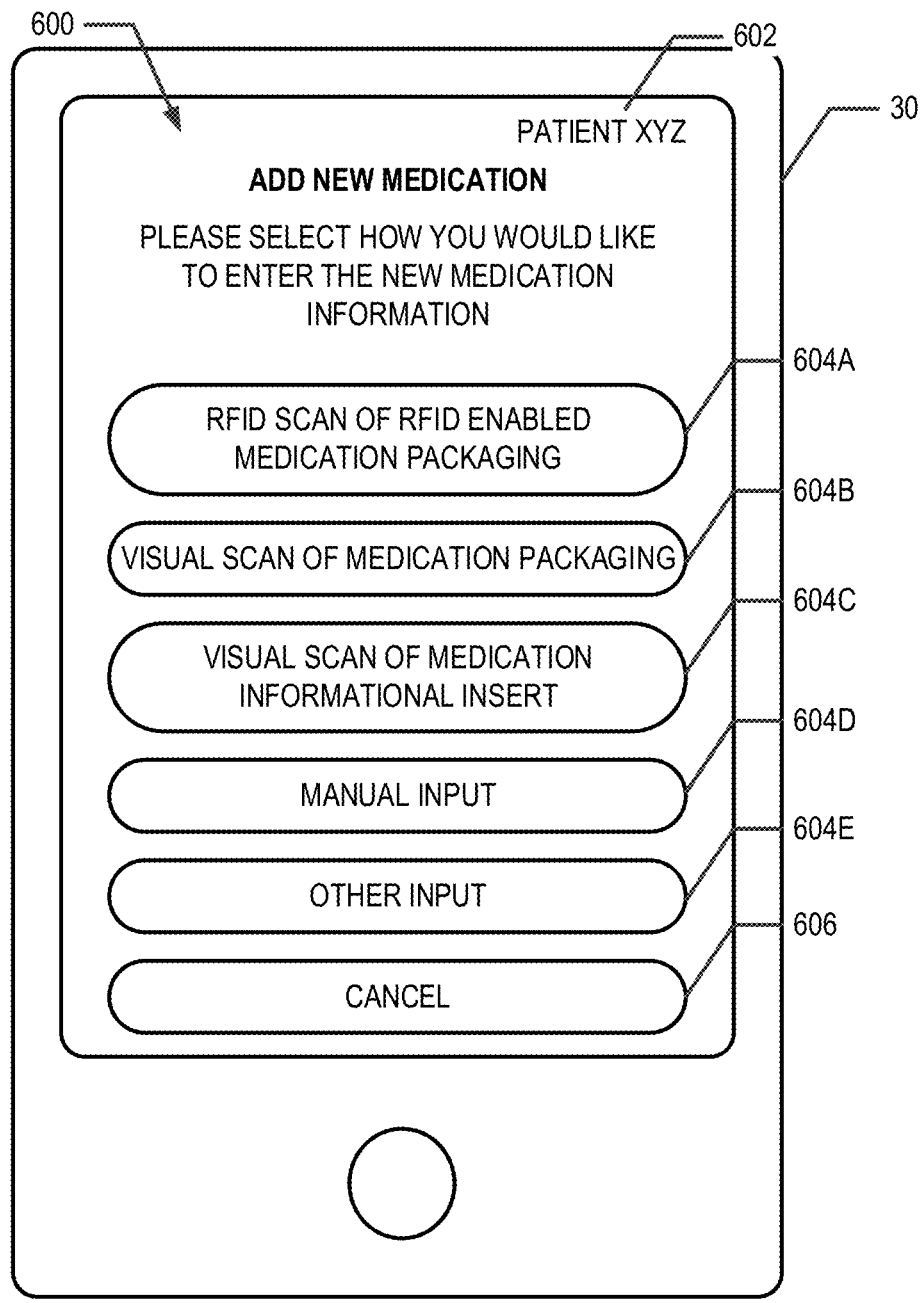
Figure 7:
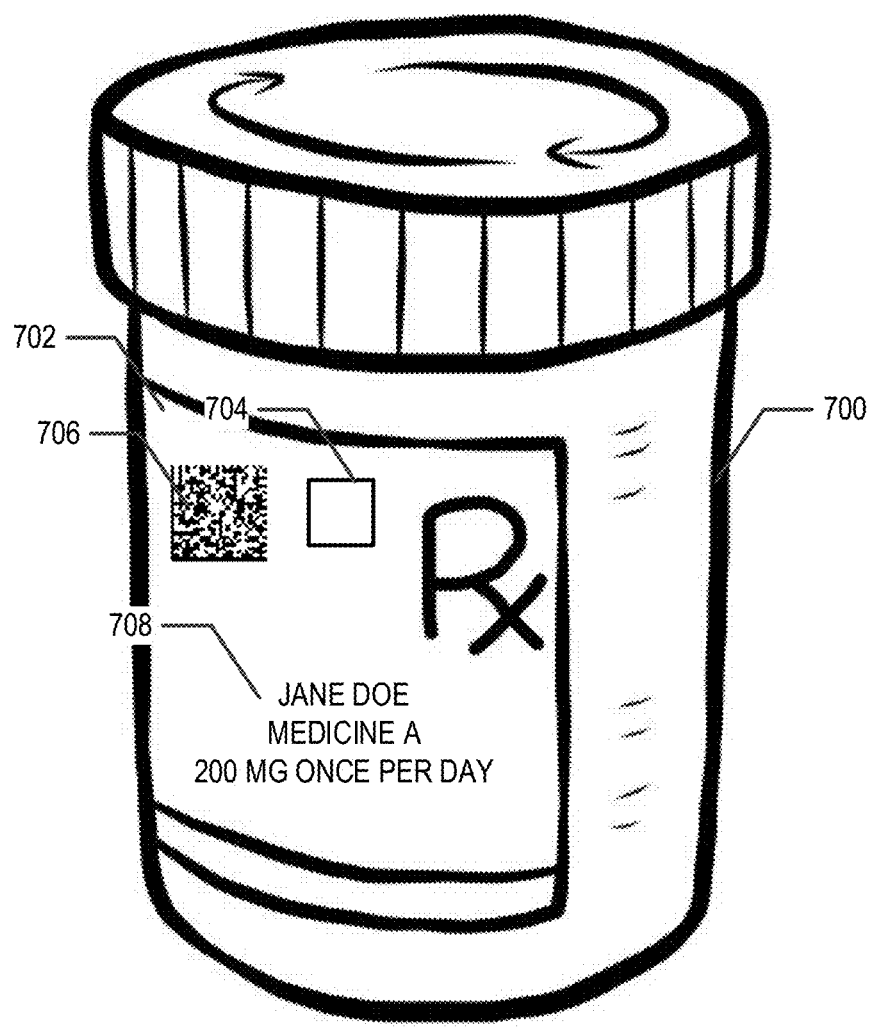
Figure 8:
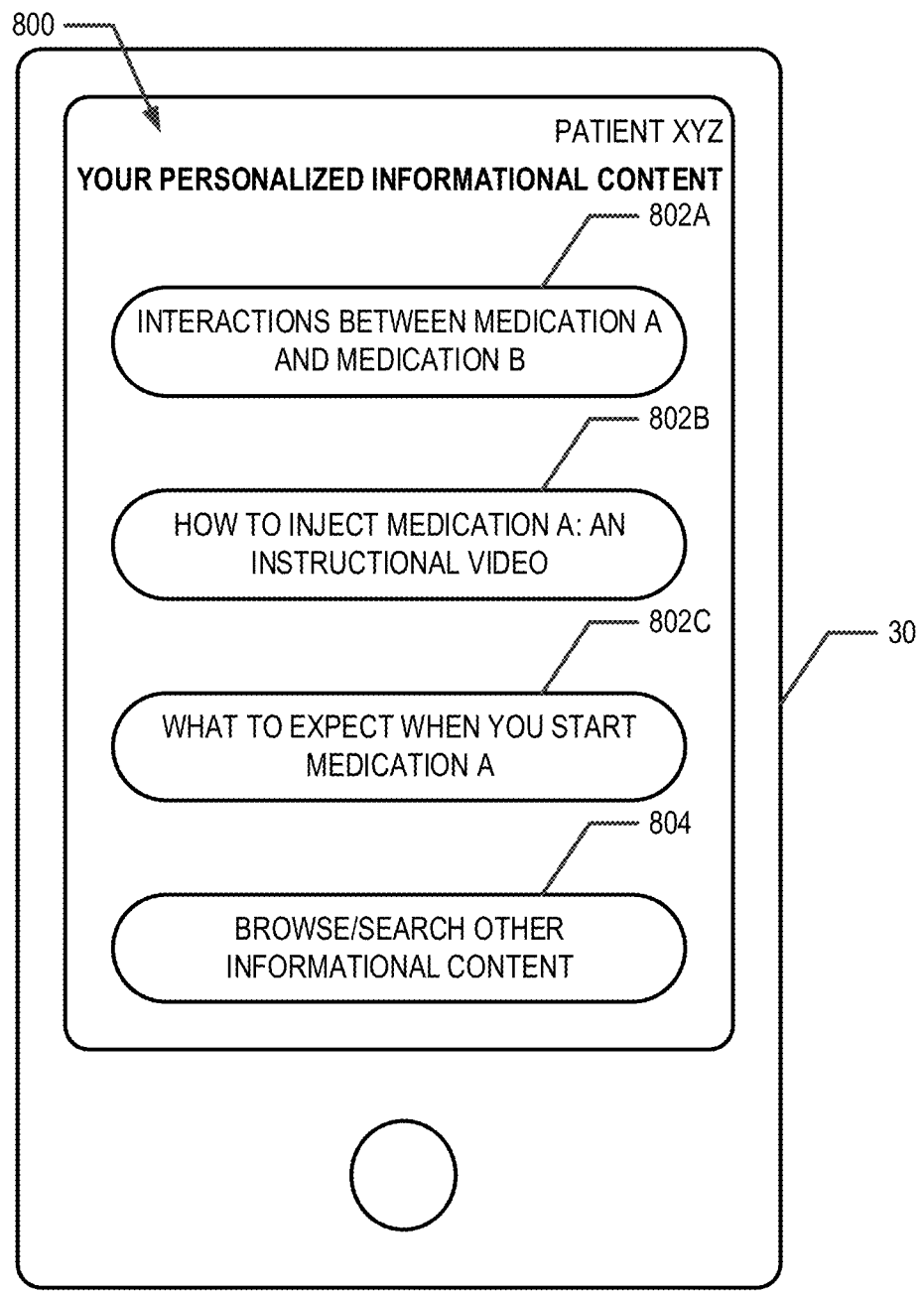
Figure 9:
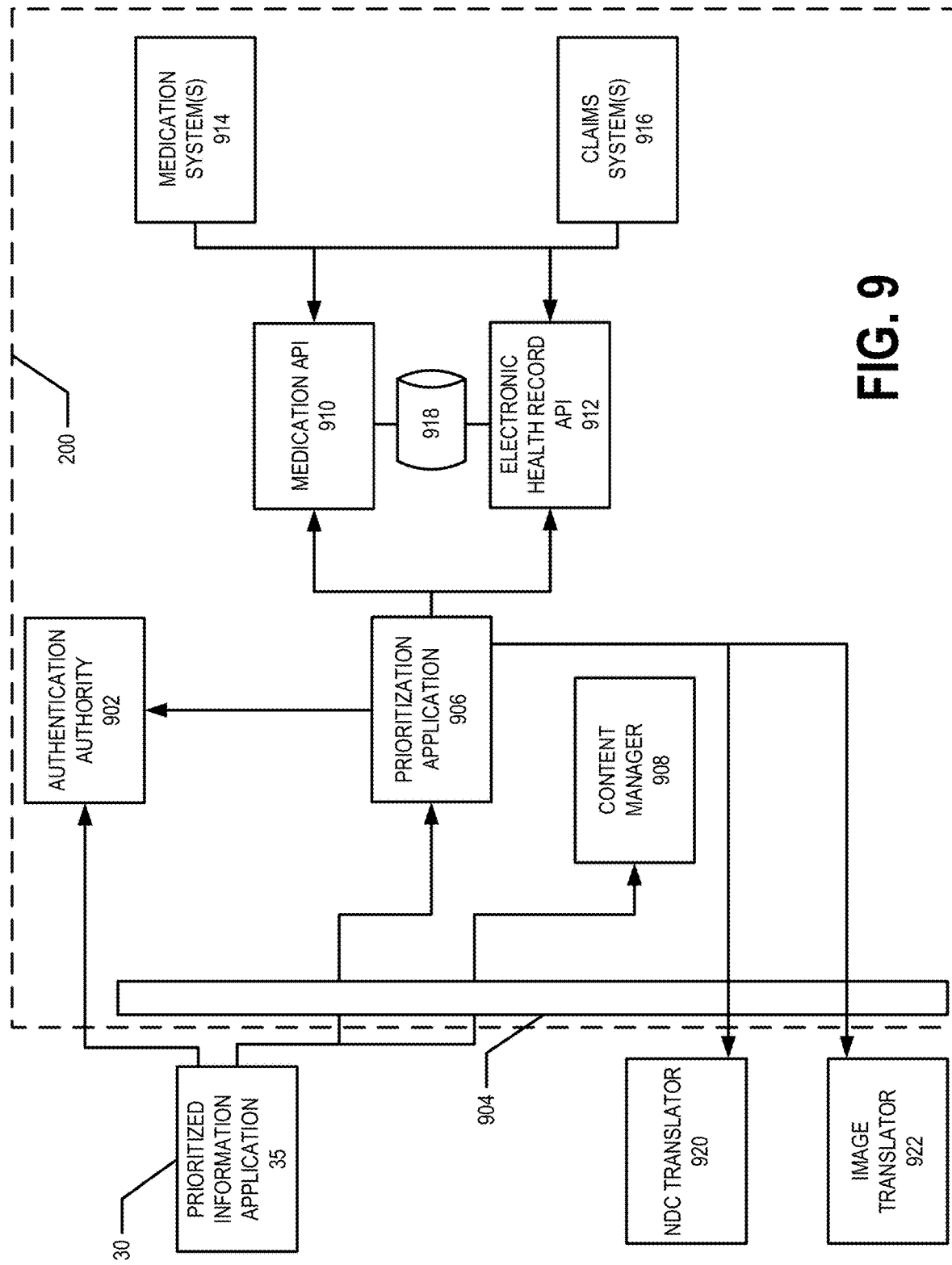

FIG. 4 provides a flowchart illustrating example procedures, processes, and/or operations performed by a prioritization computing entity to provide a user with personalized, prioritized informational content items, in accordance with an example embodiment of the present invention;

FIG. 5 provides a flowchart illustrating example procedures, processes, and/or operations performed by a user computing entity to provide a user with personalized, prioritized informational content items, in accordance with an example embodiment of the present invention;

FIG. 6 illustrates an example view of a medical information interactive user interface (IUI) with which a user may interact as part of providing new event information, in accordance with an example embodiment of the present invention;

FIG. 7 illustrates an example medication bottle, in accordance with an example embodiment of the present invention;

FIG. 8 illustrates an example view of a prioritized information IUI for providing a user with personalized, prioritized informational content items, in accordance with an example embodiment of the present invention; and FIG. 9 is a diagram of a system used to generate profile information/data and providing a user with prioritized informational content items, in accordance with an example embodiment of the present invention.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. GENERAL OVERVIEW

In various embodiments, methods, systems, apparatuses, computer program products, and/or the like are provided for providing a user with information content items that are selected and/or prioritized specifically for a user based on profile information/data stored in a user profile corresponding to the user and/or based on new event information/data provided via user interaction with an IUI. For example, a user may interact with a prioritized information IUI to provide new event information/data regarding a new medication (e.g., prescription medication, over the counter medication, medical device, physical therapy, chemical therapy, occupational therapy, and/or other drug/therapy) that the user has been prescribed, is taking/using, or is planning to take/use; and/or procedure that the user has undergone and/or is expected to undergo (e.g., in-patient surgery, out-patient surgery, and/or the like). The new event information/data may be used, in accordance with profile information/data stored in a user profile corresponding to the user, to select, identify, prioritize, and/or the like one or more of a plurality of informational content items stored in an informational content data store. For example, the one or more of the plurality of informational content items may be selected, identified, prioritized, and/or the like such that the informational content items most relevant to a user's current situation (e.g., beginning a new medication, recovering from a procedure, planning to undergo a procedure) may be provided to the user. In various embodiments, the user is a patient and/or an agent of a patient (e.g., caregiver, guardian, healthcare provider, and/or the like) and the user profile corresponds to the patient such that the profile information/data stored in the user profile comprises information/data corresponding to medical events and/or other events corresponding to the patient. For example, the informational content items most relevant to the user's current situation may be prominently provided (e.g., via the prioritized information IUI) such that the user may easily and readily access the informational content items most relevant to the user.

In various embodiments, an informational content item may comprise an article or other textual presentation of information, one or more images, one or more videos, one or more audio tracks, and/or various combinations thereof. In an example embodiment, each informational content item is associated with one or more content indicators. For example, a content indicator may provide information/data regarding the information/data provided by an informational content item. For example, an informational content item may comprise information/data regarding drug interactions between a first drug and one or more second drugs and/or a class/type of drug and the content indicators may indicate that the informational content item corresponds to the first drug and each of the one or more second drugs and/or the class/type of drug. Thus, if a user is starting to take the first drug and, according to the corresponding user profile, is already taking one of the one or more second drugs and/or a drug of the class/type of drug discussed by the informational content item, it may be determined that the informational content item is relevant to the user and/or of high priority for the user. In various embodiments, the content indicators may correspond to medications and/or classes/types of medication, procedures, known allergies, family history, user age, user medical history, user geographical location, medical codes (e.g., prescription codes, procedure codes, diagnosis codes, and/or the like), and/or the like. In various embodiments, the content indicators may comprise flags, tags, keywords, and/or the like. In an example embodiment, the plurality of informational content items are associated with an order such that the order of the informational content items deemed to be relevant to a user determines the priority of the informational content items with respect to the user. In an example embodiment, the each content indicator is associated with and/or assigned a weight such that the aggregated weight of content indicators of an informational content item matched to the new event information and/or profile information/data stored in the corresponding user profile determines the priority of the informational content item for the user.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

Figure 1:
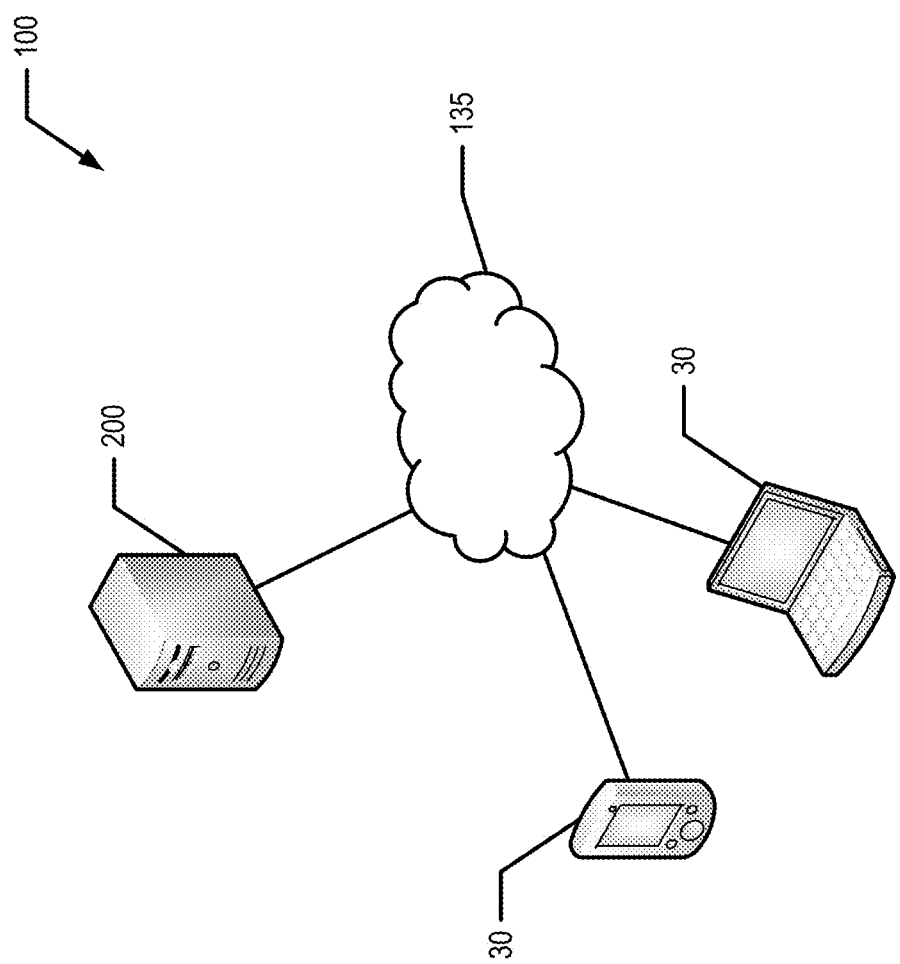
FIG. 1 is a diagram of a system that can be used to practice various embodiments of the present invention.

FIG. 1 provides an illustration of a system 100 that can be used in conjunction with various embodiments of the present invention. As shown in FIG. 1, the system 100 may comprise one or more prioritization computing entities 200, one or more user computing entities 30, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Prioritization Computing Entity

Figure 2:
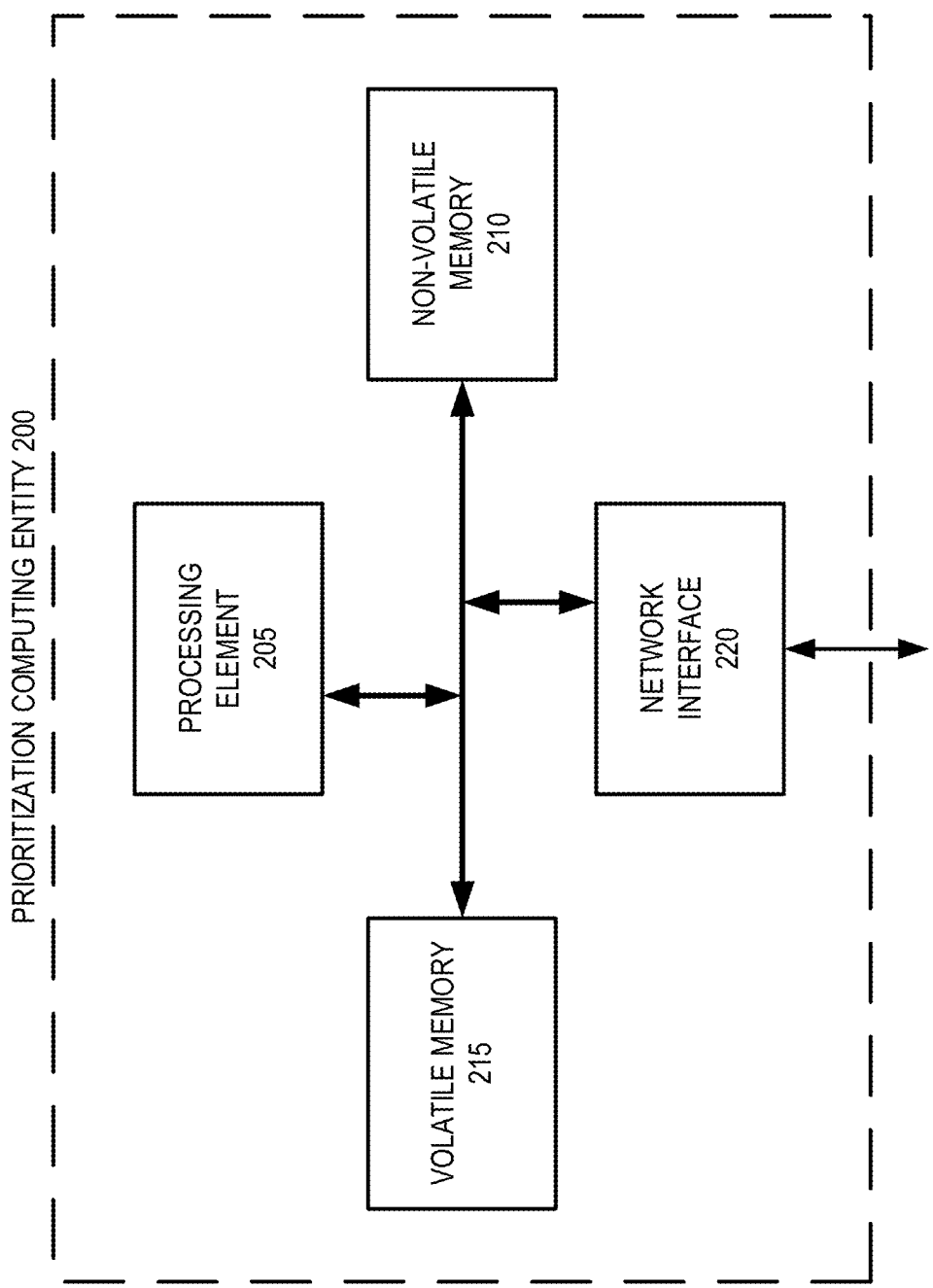
FIG. 2 is a schematic of a prioritization computing entity in accordance with certain embodiments of the present invention.

FIG. 2 provides a schematic of a prioritization computing entity 200 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

In various embodiments, a prioritization computing entity 200 is configured to store (e.g., in memory 210, 215) a user profile data store comprising one or more user profiles. Each user profile stores information/data corresponding to a user. In various embodiments a prioritization computing entity 200 is configured to store (e.g., in memory 210, 215) an informational content data store comprising one or more informational content items and corresponding metadata. In various embodiments, a prioritization computing entity 200 is configured to prioritize and/or select at least one informational content item for a user based on received new event information/data corresponding to a user and/or profile information/data stored in the user profile corresponding to the user.

As indicated, in one embodiment, the prioritization computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. For instance, the prioritization computing entity 200 may communicate with other prioritization computing entities 200, one or more user computing entities 30, and/or the like.

As shown in FIG. 2, in one embodiment, the prioritization computing entity 200 may include or be in communication with one or more processing elements 205 (also referred to as processors, processing circuitry, and/or similar terms used herein interchangeably) that communicate with other elements within the prioritization computing entity 200 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the prioritization computing entity 200 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database. For example, in an example embodiment, the user profile data store and/or informational content data store may be a database.

In one embodiment, the prioritization computing entity 200 may further include or be in communication with volatile media (also referred to as volatile storage, memory, memory storage, memory circuitry and/or similar terms used herein interchangeably). In one embodiment, the volatile storage or memory may also include one or more volatile storage or memory media 315 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the prioritization computing entity 200 with the assistance of the processing element 205 and operating system.

As indicated, in one embodiment, the prioritization computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. For instance, the computing entity 200 may communicate with computing entities or communication interfaces of other computing entities 200, user computing entities 30, and/or the like.

As indicated, in one embodiment, the prioritization computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the computing entity 200 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol. The computing entity 200 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the prioritization computing entity's 200 components may be located remotely from other prioritization computing entity 200 components, such as in a distributed system. Furthermore, one or more of the components may be aggregated and additional components performing functions described herein may be included in the prioritization computing entity 200. Thus, the prioritization computing entity 200 can be adapted to accommodate a variety of needs and circumstances.

b. Exemplary User Computing Entity

Figure 3:
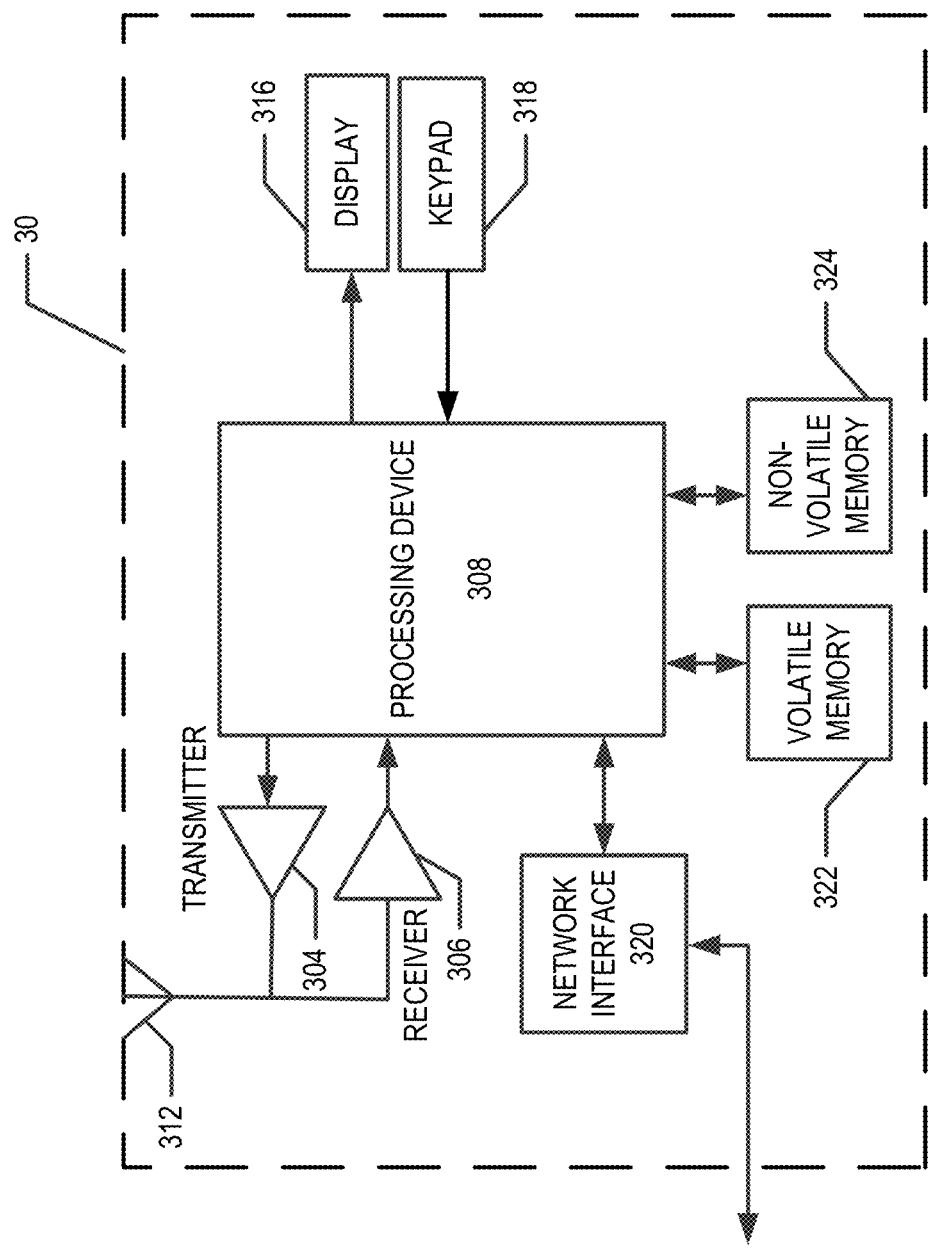
FIG. 3 is a schematic of a user computing entity in accordance with certain embodiments of the present invention.

FIG. 3 provides an illustrative schematic representative of user computing entity 30 that can be used in conjunction with embodiments of the present invention. In various embodiments, a user computing entity 30 is operated by a user. In various embodiments, a user is a user and/or an agent of a user (e.g., caregiver, guardian, healthcare provider, and/or the like). As shown in FIG. 3, a user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a prioritization computing entity 200, another user computing entity 30, a radio frequency identification (RFID) tag, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing device 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the computing entity's 200 position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface device comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, IUI, dashboard, webpage, and/or similar words used herein interchangeably executing on and/or accessible via the user computing entity 30 to cause display or audible presentation of information/data and for user interaction therewith via one or more user input interfaces. The user input interface can comprise any of a number of devices allowing the user computing entity 30 to receive data, such as a keypad 318 (hard or soft), a touch display, voice/speech or motion interfaces, scanners, readers, image capturing devices for capturing digital image information/data, or other input device. In embodiments including a (hard and/or soft) keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, any two or more of the illustrative components of the architecture of FIG. 1 may be configured to communicate with one another via respective communicative couplings to one or more networks 135. The networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

IV. EXEMPLARY SYSTEM OPERATION

In the digital age, the Internet and other data streams and sources provide nearly infinite information/data regarding various subjects. The shear amount of available information/data regarding various topics (including medications, medical procedures, and/or the like) may be overwhelming to a user (e.g., a user and/or an agent of the user) and may prevent the user from accessing, viewing, and/or receiving the information/data most relevant to the user regarding the topic. When a topic relates to medical information/data (e.g., regarding a medication and/or medical procedure) there may be information/data regarding the topic that is of particular importance to the user based on, for example, other medications the user is taking, diagnosis of the user, family history of the user, known allergies of the user, and/or the like. Various embodiments of the present invention provide an improved prioritized information IUI for providing a user with informational content items that are prioritized based on the relevancy of the informational content items to the corresponding user.

In various embodiments, a prioritization computing entity 200 may store an informational content data store (and/or may have access to an informational content data store) comprising a plurality of informational content items. In various embodiments, each informational content item may be stored in association with metadata. In an example embodiment, the metadata may comprise an order indicator (e.g., indicating the order of the corresponding informational content item in an ordered series of informational content items), one or more weights, one or more content indicators (e.g., tags, flags, keywords, topic codes, prescription codes, diagnosis codes, procedure codes, and/or combinations thereof indicating topics and/or combinations of topics to which the informational content item is relevant), one or more timing indicators (e.g., indicating a timing with respect to a user beginning a medication and/or undergoing a medical procedure to which the informational content item is relevant), and/or the like.

In various embodiments, the one or more content indicators and/or timing indicators associated with an informational content item may be used to determine if an informational content item is currently relevant to the user. For example, it may be determined if information/data corresponding to the user (e.g., profile information/data stored in a user profile and/or new event information/data recently provided and/or provided in real/near-real time) match one or more content indicators and/or timing indicators of an informational content item to determine if the informational content item is relevant to the user. The order indicator and/or weights may be used to determine a priority of the informational content item for the user. In an example embodiment, each content indicator and/or timing indicator is associated with a weight and the combined and/or aggregated weight of the content indicators and/or timing indicators that are matched with the information/data corresponding to the user determines a priority weight for the informational content item. In an example embodiment, the order indicators of the relevant informational content items (the informational content items that are matched to the information/data corresponding to the user based on the content and/or timing indicators) determines the priority of relevant informational content items for the user.

In various embodiments, a prioritization computing entity 200 may store a user profile data store (and/or have access to a user profile data store) comprising a plurality of user profiles each corresponding to a user. As should be understood, the user profile data store may be encrypted, store encrypted information/data and/or the like and access to information/data therein may be controlled to ensure the privacy and/or confidentiality of users' medical information/data. In various embodiments, a user profile stores profile information/data. In various embodiments, the profile information/data may comprise user identifying information/data (e.g., name, social security number, date of birth, a user identifier configured to uniquely identify the user, and/or the like); user contact information/data (e.g., phone number, email address or other electronic address, mailing address, billing address, and/or the like); user demographic information/data; event information/data corresponding to events related to the user (e.g., medical events such as medications taken and/or to be taken, procedures undergone or expected to be undergone, and/or the like); user medical information (e.g., medical claims information/data, physician notes, prescription codes, diagnosis codes, procedure codes, medical history information/data, known allergy information/data, family history information/data, and/or the like); user preferences regarding how, when, where, etc. informational content items are provided; access authorization information/data (e.g., a user name and/or password/personal identification number/etc. used to authenticate a user for providing new event information/data and/or receiving prioritized informational content items for the user); and/or other information/data corresponding to the user. In an example embodiment, a user profile may store an array of content item identifiers, each configured to identify an informational content item, which indicates which informational content items have been provided to a user associated with the user such that the user is not repeatedly shown the same informational content items. In various embodiments, a user profile may be updated when new event information/data is received. In various embodiments, the new event information/data is received from a prioritized information application operating on a user computing entity 30 corresponding to the user or from another computing entity (e.g., based on the processing of medical insurance claim information/data, medical information/data submitted by a provider, and/or the like). The profile information/data stored in the user profile may be used to determine which informational content items stored in the content item data store are relevant to the user.

In various embodiments, the user may access provided informational content items and/or provide new event information/data via a prioritized information application operating on a user computing entity 30. In various embodiments the prioritized information application may be a dedicated application (and/or module thereof) stored on and/or operated by the user computing entity 30, a web portal and/or website accessed via a web browser operated by the user computing entity 30, and/or the like. In various embodiments, the prioritized information application is configured to provide a prioritized information IUI via which the user may provide new event information/data and/or receive, view, and/or the like prioritized informational content for the user. In an example embodiment, the prioritized information IUI may be configured to enable a user to capture new event information/data via an RFID scan of an RFID tag secured and/or attached to medication packaging, user instructions (e.g., a folder with discharge instructions and/or procedure preparation instructions, and/or the like). In an example embodiment, the prioritized information IUI may be configured to enable a user to capture new event information/data by capturing digital image information/data of a barcode on medication packaging or a medication informational insert/handout and/or another portion of the medication packaging or a medication and/or procedure informational insert/handout (e.g., a portion including a name of medication, dosage information, and/or the like). In an example embodiment, the prioritized information IUI may be configured to enable a user to manually provide new event information/data.

Various embodiments of the present invention provide an improved IUI that simplifies the process of accessing informational content items that are relevant to a user and of high priority for a user. As should be understood, various embodiments of the present invention provide technical solutions to a technical problem that is rooted in computer networks and the Internet.

a. Exemplary Operation of a Prioritization Computing Entity

FIG. 4 provides a flowchart illustrating processes, procedures, and/or operations that may be performed by a prioritization computing entity 200 for providing a user with informational content items that are prioritized for a user based on new event information/data and/or profile information/data stored in a user profile corresponding to the user. Starting at block 402, the informational content data store is stored. For example, the prioritization computing entity 200 may store the informational content data store. For example, the prioritization computing entity 200 may comprise means, such as the processing element 205, memory 210, 215, and/or the like, for storing the informational content data store. In an example embodiment, one or more informational content items of the informational content data store are stored by a computing entity other than the prioritization computing entity 200. For example, metadata corresponding to the informational content item and including a universal location identifier (URI) for the informational content item may be stored in the informational content data store while the informational content item itself is stored by another computing entity (e.g., such that it is available via the URI included in the corresponding metadata). In various embodiments, the informational content data store may be updated periodically, regularly, in response to receiving a report that one or more informational content items have been updated, added and/or identified, and/or the like.

At block 404, a user profile may be stored. For example, the prioritization computing entity 200 may store the user profile in a user profile data store. For example, the prioritization computing entity 200 may comprise means, such as the processing element 205, memory 210, 215, and/or the like, for storing the user profile in a user profile data store. In various embodiments, a user profile may be initiated based on new event information/data received from a prioritized information application operating on the user computing entity 30 and/or other event information/data provided by another computing entity (e.g., a computing entity configured for processing medical insurance claims and/or the like). In an example embodiment, the user profile may be updated by incorporating new event information/data provided by the prioritized information application operating on the user computing entity and/or another computing entity (e.g., based on the processing of claims information/data, and/or the like). In an example embodiment, when a user profile is initiated the user profile is assigned a unique user identifier configured to uniquely identify the user profile corresponding to the user. For example, the user identifier may be a username and/or may be associated with a username such that when a user logs in to the prioritized information application using the username, the user is determined to correspond to the user profile associated with the user identifier. In an example embodiment, the user identifier is the username corresponding to and/or associated with the user profile.

At block 406, new event information/data is received. For example, the prioritization computing entity 200 may receive new event information/data. For example, the prioritization computing entity 200 may comprise means, such as processing element 205, network interface 220, and/or the like, for receiving new event information/data. For example, the new event information/data may comprise a user identifier and information/data corresponding to a medication (e.g., a new medication) that the user is taking and/or is to take, a procedure the user has undergone and/or is expected to undergo, and/or other medical information/data. In various embodiments, the prioritization computing entity 200 may receive the new event information/data, register and/or process the new event information/data, and responsive to the registering and/or processing of the new event information/data, trigger the updating of the corresponding user profile and/or a determination/identification of informational content items that are relevant to the user and prioritization thereof.

In an example embodiment, the receipt of the new event information/data may trigger the determination of the priority of the informational content items for the user. In an example embodiment, the determination of the priority of the informational content items for the user may be triggered regularly, periodically, and/or the like (e.g., once a day, once a week, once every other week, once a month, and/or the like). In an example embodiment, prior to determining the priority of the informational content items for the user, the current user state may be determined, received, and/or the like. In an example embodiment, the current user state comprises one or more instances of biometric information/data. For example, the current user state may comprise the user's blood pressure, heart rate, activity level (e.g., number of steps over the past hour, two hours, twenty-four hours, and/or the like), blood sugar level, and/or other biometric information/data. For example, the user may wear a smart device (e.g., an Internet and/or network (e.g., Wi-Fi) enabled watch and/or other device configured capture biometric information/data of the user). In an example embodiment, the prioritization computing entity 200 may communicate with the smart device to cause the biometric information/data to be captured and/or provided to the prioritization computing entity 200. In an example embodiment, the smart device is a user computing entity 30. In an example embodiment, the prioritization computing entity 200 may use the user state as new event information/data. For example, the priority of the informational content items for the user may be determined, at least in part, based on the user state (e.g., current and/or recent biometric information/data for the user).

At block 408, a priority of the informational content items for the user may be determined. For example, the prioritization computing entity 200 may determine a priority of the informational content items for the user. For example, the prioritization computing entity 200 may comprise means, such as processing element 205, memory 210, 215, and/or the like, for determining a priority of the informational content items for the user. For example, the priority of the informational content items for the user may be determined based on the new event information/data and/or profile information/data stored in the user profile. In an example embodiment, the user profile corresponding to the user may be identified and/or accessed from the user profile data store using the user identifier provided with, as part of, and/or corresponding to the new event information/data.

In various embodiments, the priority of the one or more informational content items may be determined by first identifying informational content items that are relevant to the user and then prioritizing the relevant informational content items. In various embodiments, a global priority of one or more informational content items has been determined and the relevant informational content items are identified to determine the priority of the informational content items for the user. In various embodiments, the identification of relevant informational content items and the corresponding priority of the relevant informational content items is determined as a single step. In various embodiments, the determination and/or identification of informational content items that are relevant to a user is made by matching the new event information/data and/or profile information/data stored in the user profile with content indicators and/or timing indicators associated with informational content items. For example, an informational content item may be considered relevant to a user if at least one content indicator and/or timing indicator associate with the informational content item matches the new event information/data and/or profile information/data stored in the user profile. In an example embodiment, an informational content item may be considered relevant to a user if at least a threshold number of content indicators and/or timing indicators associate with the informational content item matches the new event information/data and/or profile information/data stored in the user profile.

Each informational content item of the plurality of informational content items of the informational content data store is associated with metadata. In an example embodiment, the metadata comprises content indicators. For example, each informational content item may be associated with one or more content indicators. For example, a content indicator may provide information/data regarding the information/data provided by and/or a topic discussed by an informational content item. For example, an informational content item may comprise information/data regarding drug interactions between a first drug and one or more second drugs and/or a class/type of drug and the content indicators may indicate that the informational content item corresponds to the first drug and each of the one or more second drugs and/or the class/type of drug. Thus, if a user is starting to take the first drug and, according to the corresponding user profile, is already taking one of the one or more second drugs and/or a drug of the class/type of drug discussed by the informational content item, it may be determined that the informational content item is relevant to the user and/or of high priority for the user. In various embodiments, the content indicators may comprise flags, tags, keywords, and/or the like. In an example embodiment, the metadata associated with an informational content item may comprise a timing indicator. For example, the timing indicator may indicate a time period with relation to one or more topics, medications, procedures, and/or the like to which the information/data of the informational content item is relevant. In an example embodiment, one or more content indicators may be associated with a timing indicator. For example, if the content indicator indicates that an informational content item is discusses what to expect in the second week of recovering from knee surgery, the associated timing indicator may indicate that the most relevant time period for the providing a user who is and/or has undergone knee surgery is 5-8 days after the surgery takes place. Thus, if the user underwent knee surgery four weeks ago, the informational content item discussing the second week of recovering from knee surgery is not considered relevant to the user and would not be given a high priority. By matching the content indicators and/or timing indicators within information/data provided by the new event information/data and/or the profile information/data stored in the user profile, informational content items that are relevant to a user may be identified, selected, and/or prioritized.

In an example embodiment, the content indicators associated with one or more informational content items may be matched to the new event information/data and/or profile information/data stored in the user profile. As noted above, in an example embodiment, the content indicators may be tags and/or flags. In an example embodiment, the new event information/data may be processed (e.g., by the prioritized information application operating on the user computing entity 30 and/or a program or application operating on the prioritization computing entity 200) to generate and/or associate one or more tags or flags indicating the content and/or topics of the new event information/data. Such tags of flags may be stored in association with and/or as part of the profile information/data in the user profile. Thus, in an example embodiment, the matching of the content indicators with the new event information/data and/or the profile information/data stored in the user profile comprises matching tags or flags and/or determining which informational content items have tags or flags in common with the new event information/data and/or the profile information/data stored in the user profile. In an example embodiment, the new event information/data may be processed (e.g., by the prioritized information application operating on the user computing entity 30 and/or a program or application operating on the prioritization computing entity 200) to determine and/or identify keywords and/or medical codes corresponding to the new event information/data. Such keywords and/or medical codes may be stored in association with and/or as part of the profile information/data in the user profile. Thus, in an example embodiment, the matching of the content indicators with the new event information/data and/or the event information/data stored in the user profile comprises matching content indicators corresponding to keywords and/or medical codes (e.g., prescription codes, procedure codes, diagnosis codes, and/or the like) with the keywords and/or medical codes corresponding to the new event information/data and/or the profile information/data stored in the user profile. In various embodiments, other processes may be used for matching the content indicators to the new event information/data and/or profile information/data stored in the user profile.

In an example embodiment, the timing indicators associated with one or more content indicators and/or informational content items may be matched to the new event information/data and/or profile information/data stored in the user profile. In an example embodiment, the new event information/data may comprise a date and/or other timing indicator. For example, if a user provides new event information/data corresponding to a medication, it may be assumed that the user is starting the medication today (unless the profile information/data of the user profile indicates that the user is already taking that medication at the same dosage). If the new event information/data indicates that the user is expected to undergo and/or has undergone a medical procedure, the date of the procedure may be indicated in the new event information/data. The dates corresponding to medications and/or procedures may be stored in the user profile in association with the information/data corresponding to the medication and/or procedure, in an example embodiment. Based on the dates and/or other timing information/data of the new event information/data and/or the profile information/data stored in the user profile, timing indicators associated with one or more content indicators may be matched to the new event information/data and/or the profile information/data stored in the user profile. In an example embodiment, a content indicator may correspond to both a topic and a timing. For example, a content indicator may correspond to two weeks after knee surgery. Thus, in an example embodiment, a content indicator may be both a content indicator and an associated timing indicator such that a separate matching of the timing indicator to the new event information/data and/or the profile information/data stored in the user profile is not performed.

In various embodiments, each content indicator and/or timing indicator may be associated with a weight. In an example embodiment, combinations of content indicators and/or timing indicators may be associated with a weight. For example, an informational content item may discuss side effects and interactions for a first drug. If the new event information/data indicates that the user is starting to take the first drug, a first content indicator associated with a first weight and corresponding to the first drug may match the new event information/data. If the informational content item discusses that the first drug is likely to have a serious interaction with a second drug and unlikely to have an interaction with a third drug. The content indicators associated with the informational content item may therefore comprise a second content indicator associated with a second weight and corresponding to the second drug and a third content indicator associated with a third weight and corresponding to the third drug. In various embodiments, first weight may be larger than the second and/or third weights as the informational content item primarily concerns the first drug. In an example embodiment, the second weight may be larger than the third weight as the first drug is more likely to interact negatively with the second drug than with the third drug. Thus, if a user is starting to take the first drug and is already taking the second drug (as indicated by the new event information/data and/or profile information/data stored in the user profile), the first informational content item may be determined to be relevant to the user and to have a prioritization weight determined by aggregating (e.g., summing) the first weight and the second weight. In an example embodiment, the informational content item that is relevant to the user that has the largest prioritization weight is determined to be of the highest priority for the user. For example, if a first informational content item is determined to have a first prioritization weight for the user and a second informational content item is determined to have a second prioritization weight for the user, if the first prioritization weight is larger than the second prioritization weight, then the first informational content item is of higher priority for the user than the second informational content item.

In an example embodiment, the plurality of informational content items of the informational content data store are associated with an order. In an example embodiment, the order is a global order (e.g., all of the plurality of informational contents may be ordered into a single series or sequence). In an example embodiment, the plurality of informational content items are organized into classes or topics and ordered within the class or topic. In an example embodiment, the prioritizing of the informational content items for the user comprises determining which informational content items are relevant to the user and the order of the relevant informational content items determines and/or provides the priority of the relevant informational content items for the user.

Some non-limiting examples of how informational content items may be prioritized in various embodiments include: (a) if a user is male, then a warning to consult your doctor if you think you may be expecting, may be determined to be of low priority; (b) if a user has hypertension (e.g., as indicated by the profile information/data stored in the user profile corresponding to the user), and the medication indicated by the new event information/data may exacerbate the user's hypertension, then an informational content item regarding the possibility of the medication exacerbating hypertension may be determined to be of high priority; (c) if a user is taking multiple medications, as indicated by the new event information/data and/or the profile information/data stored in the user profile corresponding to the user, and at least some of the medications need to be taken at different times, then an informational content item regarding the taking of the medications at different times may be determined to be of high priority; (d) if a user is taking a new medication, as indicated by the new event information/data, that may result in nausea, and has a history of being prescribed anti-nausea medications, as indicated by the profile information/data stored in the user profile corresponding to the user, an informational content item describing side effects of the new medication may be determined to be of high priority; (e) if a user received crutches, as indicated by the new event information/data, and has had a history of shoulder injury, as indicated by the profile information/data stored in the user profile corresponding to the user, and informational content item regarding proper placement and utilization of the crutches may be determined to be of high priority; (f) if a user who has sleep apnea and who has had history of chronic infection, as indicated by the profile information/data of the user profile corresponding to the user, recently received a CPAP machine, as indicated by the new event information/data, an informational content item regarding suitably sanitizing the CPAP machine may be determined to be of high priority; and (g) if a user has received sutures in the emergency room, as indicated by the new event information/data, but has no history of infection or sutures, as indicated by the profile information/data stored in the user profile corresponding to the user, an informational content item regarding signs for identifying site infection (i.e. redness, fever or swelling) may be determined to be of high priority for the user.

At block 410, at least a portion of the prioritized informational content items are provided. For example, the prioritization computing entity 200 may provide at least a portion of the prioritized informational content items. For example, the prioritization computing entity 200 may comprise means, such as processing element 205, network interface 220, and/or the like, for providing at least a portion of the prioritized informational content items. For example, the prioritization computing entity 200 may transmit one or more informational content items via one or more networks such that the user computing entity 30 may receive the informational content items. In an example, the highest priority informational content item is provided. In an example embodiment, the n highest priority informational content items are provided. For example, the two or three highest priority informational content items are provided. In various embodiments, the informational content items may be provided to the user via a content distribution network (CDN).

At block 412, the user profile is updated to reflect the new event information/data. For example, the prioritization computing entity 200 may update the user profile to reflect and/or include the new event information/data. For example, the prioritization computing entity 200 may comprise means, such as processing element 205, memory 210, 215, and/or the like, for updating the user profile. For example, the user profile identified and/or accessed using the user identifier of the new event information/data may be updated to include the new event information/data.

In an example embodiment, the prioritization computing entity 200 provides one or more prioritized informational content items to a user computing entity 30 for provision to the user in response to receiving new event information/data. In an example embodiment, the prioritization computing entity determines, identifies, and/or selects and provides one or more prioritized informational content items to a user computing entity 30 for provision to the user periodically and/or regularly (e.g., at 8 am every day, at noon on Mondays, once a week, once a day, and/or the like). The period and/or timing of the provision of the one or more prioritized informational content items to a user computing entity 30 may be determined based on preferences stored in the user profile. The user profile may also store preferences indicating how the user would like to receive the one or more prioritized informational content items. For example, the one or more prioritized informational content items may be pushed to the user computing entity 30 such that the one or more prioritized informational content items are available via the prioritized information IUI, the one or more prioritized informational content items and/or a link thereto may be emailed or provided to another electronic address, and/or the like.

b. Exemplary Operation of a User Computing Entity

FIG. 5 provides a flowchart illustrating processes, procedures, and/or operations that may be performed by a user computing entity 30 for providing a user with informational content items that are prioritized for a user based on new event information/data and/or profile information/data stored in a user profile corresponding to the user. Starting at block 502, a prioritized information application is operated by the user computing entity 30 to provide a prioritized information IUI. For example, application program code may be stored in the memory 322, 324 that, when executed by the processing device 308, provide the prioritized information application and the corresponding prioritized information IUI. In various embodiments the prioritized information application may be a dedicated application (and/or module thereof) stored on and/or operated by the user computing entity 30, a web portal and/or website accessed via a web browser operated by the user computing entity 30, and/or the like. The prioritized information application provides a prioritized information IUI via the user interface of the user computing entity 30.

At block 504, user input indicating new event information/data is to be provided is received. For example, the user computing entity 30 may receive user input indicating a user would like to provide new event information/data for a user corresponding to the user. For example, the user computing entity 30 may comprise means, such as processing device 308, one or more input devices of the user interface, and/or the like, for receiving user input indicating a user would like to provide new event information/data for a user corresponding to the user. For example, FIG. 6 illustrates an example add new medication view 600 of a prioritized information IUI. For example, a user (e.g., operating a user computing entity 30) may log in and/or be authenticated via the prioritized information application to provide new event information/data corresponding to the user and/or receive informational content items relevant to and/or prioritized for the user. The user (e.g., operating the user computing entity 30) may then navigate to a screen, select a menu, and/or the like indicating that the user would like to provide new event information/data and, responsive thereto, be provided with the add new medication view 600 and/or another view of the prioritized information IUI configured to guide and/or aid the user in providing new event information/data. In an example embodiment, the prioritized information IUI and/or the prioritized information application are configured to guide the user through capturing medication information/data (e.g., a medication name, identifier, and/or prescription code; dosage information/data; and/or the like) from medication packaging, such as medication bottle 700 shown in FIG. 7, an informational insert provided with the medication and/or by a healthcare provider's office, and/or the like.

For example, as shown in FIG. 7, a medication bottle 700 may have a label 702 affixed thereto. In an example embodiment, the label 702 may comprise an RFID tag 704 and/or another NFC and/or short range communication chip, tag, and/or the like. In an example embodiment, an RFID tag 704 and/or another NFC and/or short range communication chip, tag, and/or the like may be affixed to the medication bottle 700 rather than to the label 702. In an example embodiment, the label 702 may comprise a barcode 706 (e.g., a one dimensional (1D) or two dimensional (2D) barcode). For example, the label 702 may comprise a Code 128, Code 39, Interleaved 2 of 5, UPCa, UPCe, EAN8, EAN13, Databar, and/or other 1D barcode; and/or a Data Matrix, QR Code, Aztec, PDF417, MaxiCode, and/or other 2D barcode 706. In an example embodiment, the medication bottle 700 may comprise human readable information/data 708. In an example embodiment, the human readable information/data 708 provides medication information/data such as the user's name, medication name, dosage information/data, and/or other information/data related to the medication and/or the user's prescription.

In various embodiments, as shown in FIG. 6, a new medication view 600 of the prioritized information IUI may comprise user identifying information 602, one or more selectable option elements 604 (e.g., 604A, 604B, 604C, 604D, 604E), a selectable cancel element 606, and/or the like. In an example embodiment, the user identifying information 602 may be the user's name and/or portion thereof, a user identifier, a username corresponding to the user profile corresponding to the user, and/or the like. The selectable cancel element 606 may be configured such that when user selection of the selectable cancel element 606 is received (e.g., via user interaction with one or more input devices of the user interface of the user computing entity 30), that the user is returned to a previous or main view, menu, and/or the like of the prioritized information application.

In various embodiments, the one or more selectable option elements 604 may comprise a RFID scan button 604A. In an example embodiment, when the user input selecting the RFID scan button 604A is registered (e.g., via user interaction with one or more input devices of the user interface of the user computing entity 30), the prioritized information application causes the transmitter 304, antenna 312, and receiver 306 (and/or another RFID transceiver and/or reader in operable communication with the processing device 308) poll and/or read any RFID tags in the vicinity of the user computing entity 30. For example, if the user is to start taking a new medication and the medication packaging (e.g., bottle, blister pack, paper carton, and/or other packaging) may have an RFID tag affixed thereto. The RFID tag may be configured to provide medication information/data (e.g., a medication name, identifier, and/or prescription code; dosage information/data; and/or the like), in an example embodiment. In an example embodiment, the medication information/data may further comprise a user's name and/or other user identifier that may be checked to ensure the user for which the new event information/data is being provided is the same user to which the medication was prescribed. In an example embodiment, the RFID tag may merely provide an RFID tag identifier that may be stored in association with medication information/data (e.g., a medication name, identifier, and/or prescription code; dosage information/data; and/or the like) in a data store (e.g., a database) stored by the prioritization computing entity 200 and/or accessible to the prioritization computing entity 200 and/or user computing entity 30 via one or more networks 135. In an example embodiment, the prioritized information application 35 operating on the user computing entity 30 is configured to communicate the information/data received and/or determined from the RFID scan to the prioritization computing entity 200 (e.g., the prioritization application 906) using a RESTful application programming interface (API). In an example embodiment, the API may be protected by a security gateway 904 (see FIG. 9) which may require a valid access token, security assertion markup language (SAML) packet, and/or the like for accessing the API. For example, a user may need to be authenticated via the prioritized information application before providing new event information/data. As should be understood, various other types of NFC and/or short range communication may be used to read, receive, and/or determine medication information/data (e.g., medication name, identifier, and/or prescription code; dosage information/data; and/or the like).

In various embodiments, the one or more selectable option elements 604 may comprise one or more visual scan buttons 604B, 604C. In an example embodiment, when the user input selecting a visual scan button 604B, 604C is registered (e.g., via user interaction with one or more input devices of the user interface of the user computing entity 30), the prioritized information application causes an image capturing device of the user computing entity 30 (e.g., a digital camera, barcode scanner, and/or the like) to be activated to capture digital image data. In an example embodiment, the user may capture digital image data comprising a one dimensional or two dimensional barcode on the packaging of a medication, an informational insert provided with a medication (e.g., provided by the pharmacy), and/or the like. In an example embodiment, the user may capture digital image data comprising a label of the medication packaging, a portion of the informational insert comprising the medication information/data (e.g., medication name and/or dosage information/data, and/or the like). The user computing entity 30 (and/or the prioritization computing entity 200) may analyze the captured digital image information/data to extract and/or access medication information/data (e.g., a medication name, identifier, and/or prescription code; dosage information/data; and/or the like) corresponding to the medication and the user. For example, if the digital image is of the medication packaging label, the image may be parsed to determine the medication information/data (e.g., medication name and dosage information/data). For example, if the digital image is of a 1D or 2D barcode, the barcode may encode the medication information/data (e.g., a medication name, identifier, and/or prescription code; dosage information/data; and/or the like) and/or provide and index that may be stored in association with medication information/data (e.g., a medication name, identifier, and/or prescription code; dosage information/data; and/or the like) in a data store (e.g., a database) stored by the prioritization computing entity 200 and/or accessible to the prioritization computing entity 200 and/or user computing entity 30 via one or more networks 135. In an example embodiment, the prioritized information application operating on the user computing entity 30 is configured to communicate the captured digital image information/data to the prioritization computing entity 200 using a RESTful application programming interface (API). In an example embodiment, the API may be protected by a security gateway 904 (see FIG. 9) which may require a valid access token, security assertion markup language (SAML) packet, and/or the like for accessing the API. For example, a user may need to be authenticated via the prioritized information application before providing new patient information/data.

In various embodiments, the one or more selectable option elements 604 may comprise a manual input button 604D. In an example embodiment, when the user input selecting the manual input button 604D is registered (e.g., via user interaction with one or more input devices of the user interface of the user computing entity 30), the prioritized information IUI may provide the user with a screen having one or more fillable fields that the user may enter information/data into by selecting and/or entering information/data. For example, the user may provide and/or select medication information/data (e.g., a medication name, dosage information/data, and/or the like). In various embodiments, the one or more selectable option elements 604 may comprise one or more other input buttons 604E for providing input via various other techniques.

Returning to FIG. 5, the user may then provide input providing the new event information/data and/or at least a portion thereof, at block 506. For example, via interaction with the prioritized information IUI, the user may cause new event information/data to be received by the user computing entity 30 (e.g., passed to the prioritized information application) via reading of an RFID tag, capturing and analyzing digital image data, receiving user input manually entering and/or selecting new event information/data, and/or the like. For example, the user computing entity 30 may comprise means, such as processing device 308, input devices, image capturing devices, transmitter 304, antenna 312, and receiver 306 (and/or another RFID transceiver and/or reader in operable communication with the processing device 308), and/or the like for receiving input providing the new event information/data.

At block 508, the user computing entity 30 provides the new event information/data such that the prioritization computing entity 200 may receive the new event information/data. For example, the user computing entity 30 may transmit the new event information/data via one or more networks 135. In an example embodiment, the new event information/data is provided in an encoded and/or encrypted form. The prioritization computing entity 200 may receive the new event information/data; determine, select, identify, and/or the like one or more prioritized informational content items; and provide the one or more prioritized informational content items.

At block 510, the user computing entity 30 receives the one or more prioritized informational content items provided by the prioritization computing entity 200. The one or more prioritized informational content items are then passed to the prioritized information application for provision to the user via the prioritized information IUI. At block 512, at least one of the received one or more prioritized informational content items is provided to a user via the prioritized information IUI. In an example embodiment, a push notification is provided to the user via the user computing entity 30 that new informational content is available via the prioritized information IUI. The user may then access and/or open the prioritized information application to access at least one of the received one or more prioritized informational content items via the prioritized information IUI. For example, an informational content item may comprise text, images, video, audio, and/or the like and such may be provided to the user via the appropriate output device of the user computing entity 30 (e.g., display 316, speakers, and/or the like).

FIG. 8 provides an example content selection view 800 of the prioritized information IUI. For example, the user computing entity 30 may receive three informational content items that the prioritization computing entity 200 has determined, identified, and/or selected as being relevant to the user and of high priority to the user at this time. The content selection view 800 comprises one or more selectable elements 802 (e.g., 802A, 802B, 802C) that may be selected to view a particular one of the informational content items determined, identified, and/or selected as being relevant to the user and of high priority to the user at this time. In an example embodiment, the content selection view 800 may further comprise a search/browse selectable element 804 such that the user may search or browse a collection of informational content items.

c. Generating a User Profile

In various embodiments, a user profile and/or at least a portion of the profile information/data stored in a user profile may be automatically generated. In an example embodiment, a user profile may be generated once (e.g., when a user registers with the prioritized information application, and/or the like) and stored in the user profile in the user profile data store. In an example embodiment, at least a portion of the profile information/data is generated for the determination of the prioritization of the informational content items for the user. In an example embodiment, a portion of the profile information/data may be generated as needed (e.g., to perform the prioritization of the informational content items for the user) and is not stored in the user profile data store to maintain the privacy and confidence of sensitive information/data. FIG. 9 illustrates a system that may be used to generate a user profile and/or profile information/data of a user profile for determining the priority of a plurality of informational content items for a user and providing the user with prioritized informational content items.

The prioritized information application 35 operating on the user computing entity 30 provides the user with a prioritized information IUI through which a user may interact to provide information/data such as profile information/data, new event information/data, and/or the like. In an example embodiment, before providing information/data through the prioritized information IUI, a user may be authenticated. For example, the prioritized information application 35 operating on the user computing entity 30 may communicate with an authentication agent 902 operating on the prioritization computing entity 200. For example, the user computing entity 30 may use an application programming interface (API) to perform an authentication of the user via the authentication agent 902. In an example embodiment, the authentication agent 902 may be an OpenID Connection Authorization Authority using HealthSafe ID, and/or the like. In an example embodiment, the authentication of the user may include the use of biometric information/data (e.g., user's pupil, face, fingerprint, and/or the like); a password, personal identification number, and/or the like; and/or other authentication information/data.

In an example embodiment, the authentication agent 902 returns an access token to the prioritized information application 35 operating on the user computing entity 30. For example, the access token may identify the user and/or enable the prioritized information application 35 to communicate with the prioritization application 906 operating on the prioritization computing entity 200 using encrypted communications. For example, new event information/data submitted to the prioritization application 906 by the prioritized information application 35 may comprise the access token. For example, the access token may be used to provide a user identifier as part of the new event information/data. In an example embodiment, the prioritized information application 35 operating on the user computing entity 30 may verify the access token and extract a user identifier corresponding to the user from the payload of the access token. In an example embodiment, the prioritized information application 35 operating on the user computing entity 30 may communicate with the prioritization application 906 (and/or the content manager 908) operating on the prioritization computing entity 200 through a security gateway 904 using the access token.

In an example embodiment, the prioritization application 906 determines a priority of a plurality of informational content items for a user. For example, the prioritization application 906 operating on the prioritization computing entity 200 may perform processes, procedures, operations, and/or the like corresponding to blocks 406, 408, and/or 410 of FIG. 4. For example, the prioritization application 906 may be configured to receive new event information/data and determine a priority of a plurality of informational content items for a user. In various embodiments the prioritization application 906 may communicate with a national drug code (NDC) translator 920 and/or image translator 922 operating on the prioritization computing entity 200 and/or another computing entity for extracting new event information/data from digital image information/data provided by a user computing entity 30. For example, if a user captures digital image data comprising a barcode, new event information/data comprising the barcode and/or a digital representation thereof, may be provided to the prioritization application 906 operating on the prioritization computing entity 200 by the prioritized information application 35 operating on the user computing entity 30. If the prioritization application 906 determines the barcode corresponds to a prescription drug, the prioritization application 906 may communicate with the NDC translator 920 to extract an NDC number for the corresponding medication. If the prioritization application 906 determines the barcode does not correspond to a prescription drug, a database such as a Universal Product Code (UPC) database may be accessed to retrieve information/data corresponding to the medication. In another example example, if a user captures digital image information/data of a label and/or other portion of a medication, new event information/data comprising the digital image information/data may be provided to the prioritization application 906 operating on the prioritization computing entity 200 by the prioritized information application 35 operating on the user computing entity 30. The prioritization application 906 may communicate with the image translator 922 to extract a medication name, dosage, NDC, and/or the like for the medication. In an example embodiment, a user may capture digital image information/data comprising a QR Code (e.g., an example of a 2D barcode) and new event information/data comprising the digital image information/data may be provided to the prioritization application 906 operating on the prioritization computing entity 200 by the prioritized information application 35 operating on the user computing entity 30. The prioritization application 906 may extract a known identifier from the digital image information/data comprising the QR Code. In an example embodiment, the known identifier may be a NDC code (e.g., if the medication is prescription drug), a universal resource identifier (URI) and/or universal resource locator (URL) (e.g., if the medication is not a prescription drug), and/or the like such that the medication may be identified.

In various embodiments, the prioritization application 906 may communicate with one or more medication systems 914 and/or a medication database stored in database 918 via a medication API 910. In an example embodiment, the medication API 910 may be configured to update and/or modify a medication database comprising information/data regarding various medications. For example, the medication database may store information/data regarding interactions information/data corresponding to interactions between medications or between a medication and another substance, dosing information/data, side effect information/data, medication usage information/data (e.g., diagnoses for which and/or situations in which the medication may be prescribed and/or used), and/or other medication information/data corresponding to medications. In various embodiments the medication API 910 may update and/or modify the medication database based on medication information/data received from one or more medication systems 914. In an example embodiment, the medication system(s) 914 provide a live stream of medication information/data to the medication API 910 which, in turn, uses the medication information/data to update the medication database. In various embodiments, the medication system(s) 914 may provide a live stream of medication information/data to the medication API 910 on a periodic and/or regular basis (e.g., every ten minutes, every thirty minutes, every hour, and/or the like). In an example embodiment, only updates and/or changes to medication information/data are provided. In various embodiments, the medication information/data provided by the medication system(s) 914 may be generated by processing medication related insurance claims, published medical studies, private medical studies, and/or the like. When the prioritization application 906 passes one or more medication names, NDC numbers, and/or other medication identifiers to the medication API 910, the medication API 910 may access the medication database and provide the prioritization application 906 with medication information/data regarding the medication corresponding to the provided one or more medication names, NDC numbers, and/or other medication identifiers.

In various embodiments, the prioritization application 906 may communicate with one or more medication systems 914 and/or claims systems 916 via an electronic health record (EHR) API 912. In an example embodiment, the EHR API 912 may be configured to update and/or modify a user profile data store comprising information/data a plurality of user profiles based on user-specific information/data received from the one or more medication systems 914 and/or claims systems 916. For example, the database 918 may be a secured and/or encrypted database comprising the user profile data store storing a plurality of user profiles each comprising profile information/data corresponding to a user. In various embodiments the EHR API 912 may update and/or modify one or more user profiles based on information/data received from one or more medication systems 914 and/or claim systems 916. In an example embodiment, the medication system(s) 914 and/or claim systems 916 provide a live stream of user-specific information/data corresponding to users to the EHR API 912 which, in turn, uses the user-specific information/data to update the profile information/data of the corresponding user profiles. In various embodiments, the medication system(s) 914 and/or claims system(s) 916 may provide a live stream of user-specific information/data to the EHR API 910 on a periodic and/or regular basis (e.g., every ten minutes, every thirty minutes, every hour, and/or the like). In an example embodiment, only updates and/or changes to user-specific information/ data are provided. In various embodiments, the user-specific information/data provided by the medication system(s) 914 and/or claims system(s) 916 may be generated by processing insurance claims and/or other user-specific health information/data (e.g., physician's notes submitted by a healthcare provider, and/or the like). When the prioritization application 906 passes personally identifiable information (PII) for a user (e.g., a user identifier, user name, and/or the like) to the EHR API 912, the EHR API 912 may access the user profile corresponding to the identified user from the user profile data store and provide the prioritization application 906 with profile information/data corresponding to the user. For example, responsive to the prioritization application 906 providing PII to the EHR API 912, the EHR API 912 may access a user profile based on the PII, and extract profile information/data from the user profile and pass the profile information/data to the prioritization application 906 for use in determining a priority for one or more informational content items for the user. In an example embodiment, the EHR API 912 may be configured to communicate with a smart device corresponding to the user to cause a current state of the user to be determined. For example, responsive to receiving PII identifying a user, the EHR API 912 may communicate with a smart device to cause the smart device to capture biometric information/data indicating a current state of the user.

In various embodiments, the medication system(s) 914 and/or claims systems 916 may operate on the prioritization computing entity 200 and/or another computing entity in secured communication with the prioritization computing entity 200 (e.g., a computing entity operating behind the security gateway 904).

In an example embodiment, responsive to receiving new event information/data that identifies a medication corresponding to a user, the prioritization application 906 may pass the information/data identifying the medication to the medication API 910 and, responsive thereto, receive medication information/data corresponding to the identified medication. The prioritization application 906 may pass information/data identifying the user to the EHR API 912 and, responsive thereto, receive profile information/data corresponding to the user. The prioritization application 906 may then use the received medication information/data profile information/data, and/or the new event information to determine which informational content items of the plurality of the informational content items are relevant to the user, determine a priority for the relevant informational content items and/or each of the plurality of informational content items, and cause at least one informational content item that is of high priority to the user to be provided to the user computing entity 30 for providing to the user via the prioritized information IUI.

In an example embodiment, the content manager 908 may be configured to manage the informational content items of the informational content data store. For example, the content manager 908 may be configured to, automatically and/or via receiving input from an administrator, generate one or more informational content items, update and/or delete one or more informational content items, and/or the like.

d. Technical Advantages

Various embodiments provide an improved IUI for providing prioritized and/or personalized informational content items to a user. In particular, example embodiments provide a technical solution to a technical problem that is rooted in the Internet. For example, various embodiments provide a particular manner presenting information by a user computing entity 30 to allow and/or enable users to easily see the most relevant and highest priority information/data for a user. As noted above the amount of information/data available to a user via the Internet is overwhelmingly large. Various embodiments of the present invention filter a plurality of informational content items in a manner that is specifically personalized for a user such that the informational content items provided to the user computing entity for provision to the user are selected to be relevant and of high priority to the user. Thus, various embodiments do not merely provide a user with access to informational content. Rather, various embodiments provide an improved TUT that provides a user with informational content that is filtered in a personalized manner to provide a user with informational content that is relevant and of high priority to a user corresponding to the user.

V. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for providing personalized and prioritized informational content to a patient, the method comprising:

authenticating, by a prioritization computing entity comprising at least one processor, one or more memories, and a network interface, a patient interacting with an interactive user interface executing on a user computing entity, wherein (a) the prioritization computing entity uses an authentication agent executing on the prioritization computing entity to authenticate the patient via first user biometric information, and (b) the first user biometric information corresponds to at least one of the patient's pupil, the patient's face, or the patient's fingerprint;

after authenticating the patient, receiving, by the prioritization computing entity, new event information corresponding to the patient, wherein (a) the new event information comprises (i) first medication information comprising machine-readable code corresponding to a medication, and (ii) a user identifier, (b) the first medication information is captured via an imaging capturing component or an RFID scanner of a user computing entity operated by the patient, and (c) the new event information is provided to the prioritization computing entity responsive to the patient interacting with the interactive user interface;

responsive to receiving the new event information:

transmitting, by the prioritization computing entity, a request for user history information for the patient, wherein (a) the request for the user history information for the patient is a first application programming interface (API) request, (b) the request for the user history information for the patient comprises the user identifier, and (c) the user history information is stored in association with a user profile, transmitting, by the prioritization computing entity, a request for second medication information, wherein (a) the request for the second medication information is a second API request, and (b) the request for the second medication information comprises at least a portion of the first medication information, and transmitting, by the prioritization computing entity, a request for real-time user state information of the patient, wherein the real-time user state information (a) is collected by (i) the user computing entity or (ii) a wearable computing entity worn by the patient and communicatively coupled to the user computing entity, (b) is collected within a configurable time period of the request for real-time user state information of the patient, and (c) comprises second user biometric information comprising one or more of real-time heart rate information, real-time blood pressure information, real-time activity level information, or real-time blood sugar level information;

receiving, by the prioritization computing entity, the real-time user state information;

based at least in part on the new event information, the second medication information, the user history information, and the real-time user state information, prioritizing, by the prioritization computing entity, a plurality of informational content items in an order determined to be relevant-for the patient, wherein: (a) the prioritization assigns a priority to each of the plurality of informational content items, and (b) the priority of a particular informational content item is determined based at least in part on: (i) whether one or more content indicators associated with the informational content item correspond to one or more content preferences described in the user history information, (ii) whether one or more timing indicators, associated with the informational content item correspond to one or more timing preferences described in the user history information, and (iii) correspondence between the informational content item and a current user biometric state as determined based on the real-time user state information;

generating and providing, by the prioritization computing entity, a presentation to the user computing entity, wherein (a) the presentation comprises a selectable user interface element for each of the plurality of informational content items prioritized for the patient, and (b) the interactive user interface simultaneously displays each of the selectable user interface elements;

responsive to receiving a user selection of one of the selectable user interface elements, retrieving, by the prioritization computing entity, from a content item data store, the content corresponding to the one of the selectable user interface elements for presentation to the patient via the interactive user interface; and transmitting, by the prioritization computing entity, content information corresponding to the one of the selectable user interface elements for updating the user profile.

2. The method of claim 1, wherein at least one of the plurality of informational content items corresponds to the medication or a medical procedure that the patient has undergone or that the patient is expected to undergo.

3. The method of claim 1, wherein each of the plurality of informational content items is associated with one or more flags, and prioritizing the plurality of informational content items for the patient is based at least in part on matching the one or more flags associated with each informational content item to at least one of the new event information, the second medication information, the user history information, and the real-time user state information.

4. The method of claim 3, wherein each of the one or more flags is associated with a weight and prioritizing the plurality of informational content items for the patient is based at least in part on the weight associated with each of the one or more flags that matches at least one of the new event information, the second medication information, the user history information, and the real-time user state information.

5. The method of claim 1, wherein prioritizing the plurality of informational content items for the patient comprises identifying, based at least in part on the order, the one or more content indicators and the one or more timing indicators, a first informational content item corresponding to at least one of the new event information, the second medication information, the user history information, and the real-time user state information.

6. The method of claim 1, wherein the machine-readable code comprises a barcode.

7. The method of claim 1, wherein the machine-readable code comprises an RFID tag.

8. An apparatus comprising at least one processor, one or more memories including computer program code for one or more programs, and a network interface, the one or more memories and the computer program code configured to, with the at least one processor, cause the apparatus to perform at least the following:
   authenticate a patient interacting with an interactive user interface executing on a user computing entity, wherein (a) an authentication agent executing on the apparatus is used to authenticate the patient via first user biometric information, and (b) the first user biometric information corresponds to at least one of the patient's pupil, the patient's face, or the patient's fingerprint;
   after authenticating the patient, receive, via the network interface, new event information corresponding to the patient, wherein (a) the new event information comprises (i) first medication information comprising machine-readable code corresponding to a medication, and (ii) a user identifier, (b) the first medication information is captured via an imaging capturing component or an RFID scanner of a user computing entity operated by the patient, and (c) the new event information is provided responsive to the patient interacting with the interactive user interface;
   responsive to receiving the new event information:
      transmit a request for user history information for the patient, wherein (a) the request for the user history information for the patient is a first application programming interface (API) request, (b) the request for the user history information for the patient comprises the user identifier, and (c) the user history information is stored in association with a user profile,
      transmit a request for second medication information, wherein (a) the request for the second medication information is a second API request, and (b) the request for the second medication information comprises at least a portion of the first medication information, and
      transmit a request for real-time user state information of the patient, wherein the real-time user state information (a) is collected by (i) the user computing entity or (ii) a wearable computing entity worn by the patient and communicatively coupled to the user computing entity, (b) is collected within a configurable time period of the request for real-time user state information of the patient, and (c) comprises second user biometric information comprising one or more of real-time heart rate information, real-time blood pressure information, real-time activity level information, or real-time blood sugar level information;
   receive the real-time user state information;
   based at least in part on the new event information, the second medication information, the user history information, and the real-time user state information, prioritize a plurality of informational content items in an order determined to be relevant for the patient, wherein: (a) the prioritization assigns a priority to each of the plurality of informational content items, and (b) the priority of a particular informational content item is determined based at least in part on: (i) whether one or more content indicators associated with the informational content item correspond to one or more content preferences described in the user history information, (ii) whether one or more timing indicators, associated with the informational content item correspond to one or more timing preferences described in the user history information, and (iii) correspondence between the informational content item and a current user biometric state as determined based on the real-time user state information;
   generate and provide a presentation to the user computing entity, wherein (a) the presentation comprises a selectable user interface element for each of the plurality of informational content items prioritized for the patient, and (b) the interactive user interface simultaneously displays each of the selectable user interface elements;
   responsive to receiving a user selection of one of the selectable user interface elements, retrieve, from a content item data store, the content corresponding to the one of the selectable user interface elements for presentation to the patient via the interactive user interface; and
   transmit content information corresponding to the one of the selectable user interface elements for updating the user profile.

9. The apparatus of claim 8, wherein at least one of the plurality of informational content items corresponds to the medication or a medical procedure that the patient has undergone or that the patient is expected to undergo.

10. The apparatus of claim 8, wherein prioritizing the plurality of informational content items for the patient is based at least in part on matching the one or more flags associated with each informational content item to at least one of the new event information, the second medication information, the user history information, and the real-time user state information.

11. The apparatus of claim 10, wherein each of the one or more flags is associated with a weight and prioritizing the plurality of informational content items for the patient is based at least in part on the weight associated with each of the one or more flags that matches at least one of the new event information, the second medication information, the user history information, and the real-time user state information.

12. The apparatus of claim 8, wherein prioritizing the plurality of informational content items for the patient comprises identifying, based at least in part on the order, the one or more content indicators and the one or more timing indicators, a first informational content item corresponding to at least one of the new event information, the second medication information, the user history information, and the real-time user state information.

13. A computer program product comprising at least one non-transitory computer-readable storage medium having computer-executable program code portions stored therein, the computer-executable program code portions comprising program code instructions, the computer program code instructions, when executed by a processor of a computing entity, are configured to cause the computing entity to at least:
   authenticate a patient interacting with an interactive user interface executing on a user computing entity, wherein (a) an authentication agent executing on the apparatus is used to authenticate the patient via first user biometric information, and (b) the first user biometric information corresponds to at least one of the patient's pupil, the patient's face, or the patient's fingerprint;
   after authenticating the patient, receive new event information corresponding to the patient, wherein (a) the new event information comprises (i) first medication information comprising machine-readable code corresponding to a medication, and (ii) a user identifier, (b) the first medication information is captured via an imaging capturing component or an RFID scanner of a user computing entity operated by the patient, and (c) the new event information is provided responsive to the patient interacting with the interactive user interface;
   responsive to receiving the new event information:
      transmit a request for user history information for the patient, wherein (a) the request for the user history information for the patient is a first application programming interface (API) request, (b) the request for the user history information for the patient comprises the user identifier, and (c) the user history information is stored in association with a user profile,
      transmit a request for second medication information, wherein (a) the request for the second medication information is a second API request, and (b) the request for the second medication information comprises at least a portion of the first medication information, and
      transmit a request for real-time user state information of the patient, wherein the real-time user state information (a) is collected by (i) the user computing entity or (ii) a wearable computing entity worn by the patient and communicatively coupled to the user computing entity, (b) is collected within a configurable time period of the request for real-time user state information of the patient, and (c) comprises second user biometric information comprising one or more of real-time heart rate information, real-time blood pressure information, real-time activity level information, or real-time blood sugar level information;
   receive the real-time user state information;
   based at least in part on the new event information, the second medication information, the user history information, and the real-time user state information, prioritize a plurality of informational content items in an order determined to be relevant for the patient,
   wherein (a) the prioritization assigns a priority to each of the plurality of informational content items, and (b) the priority of a particular informational content item is determined based at least in part on: (i) whether one or more content indicators associated with the informational content item correspond to one or more content preferences described in the user history information, (ii) whether one or more timing indicators, associated with the informational content item correspond to one or more timing preferences described in the user history information, and (iii) correspondence between the informational content item and a current user biometric state as determined based on the real-time user state information;
   generate and provide a presentation to the user computing entity, wherein (a) the presentation comprises a selectable user interface element for each of the plurality of informational content items prioritized for the patient, and (b) the interactive user interface simultaneously displays each of the selectable user interface elements;
   responsive to receiving a user selection of one of the selectable user interface elements, retrieve, from a content item data store, the content corresponding to the one of the selectable user interface elements for presentation to the patient via the interactive user interface; and
   transmit content information corresponding to the one of the selectable user interface elements for updating the user profile.

14. The computer program product of claim 13, wherein at least one of the plurality of informational content items corresponds to the medication or a medical procedure that the patient has undergone or that the patient is expected to undergo.

15. The computer program product of claim 13, wherein each of the plurality of informational content items is associated with one or more flags, and prioritizing the plurality of informational content items for the patient is based at least in part on matching the one or more flags of each content item to at least one of the new event information, the second medication information, the user history information, and the real-time user state information.

16. The computer program product of claim 15, wherein each of the one or more flags is associated with a weight, and prioritizing the plurality of informational content items for the patient is based at least in part on the weight associated with each of the one or more flags that matches at least one of the new event information, the second medication information, the user history information, and the real-time user state information.

17. The computer program product of claim 13, wherein prioritizing the plurality of informational content items for the patient comprises identifying, based at least in part on the order, the one or more content indicators and the one or more timing indicators, a first informational content item corresponding to at least one of the new event information, the second medication information, the user history information, and the real-time user state information.

* * * * *

UNITED STATES PATENT AND TRADEMARK OFFICE
CERTIFICATE OF CORRECTION

PATENT NO. : 11,416,567 B2
APPLICATION NO. : 16/136890
DATED : August 16, 2022
INVENTOR(S) : Hamilton, II et al.

Page 1 of 1

It is certified that error appears in the above-identified patent and that said Letters Patent is hereby corrected as shown below:

In the Claims

<u>Column 30</u>
Line 25, "relevant-for" should read --relevant for--

Signed and Sealed this
Fourth Day of October, 2022

Katherine Kelly Vidal
*Director of the United States Patent and Trademark Office*